United States Patent
Sarunic et al.

(10) Patent No.: US 10,251,549 B2
(45) Date of Patent: Apr. 9, 2019

(54) SYSTEM AND METHOD FOR DYNAMIC FOCUS CONTROL

(71) Applicants: Marinko Venci Sarunic, Burnaby (CA); Yifan Jian, Burnaby (CA); Eunice Michelle Chua Cua, Pasadena, CA (US); Sujin Lee, Seoul (KR); Dongkai Miao, Burnaby (CA)

(72) Inventors: Marinko Venci Sarunic, Burnaby (CA); Yifan Jian, Burnaby (CA); Eunice Michelle Chua Cua, Pasadena, CA (US); Sujin Lee, Seoul (KR); Dongkai Miao, Burnaby (CA)

(73) Assignee: Marinko Sarunic, Burnaby, BC (CA)

( * ) Notice: Subject to any disclaimer, the term of this patent is extended or adjusted under 35 U.S.C. 154(b) by 0 days.

(21) Appl. No.: 15/426,851

(22) Filed: Feb. 7, 2017

(65) Prior Publication Data

US 2017/0227350 A1    Aug. 10, 2017

Related U.S. Application Data

(60) Provisional application No. 62/292,361, filed on Feb. 7, 2016.

(51) Int. Cl.
*A61B 3/10* (2006.01)
*G01B 9/02* (2006.01)

(52) U.S. Cl.
CPC .......... *A61B 3/102* (2013.01); *G01B 9/02004* (2013.01); *G01B 9/02058* (2013.01); *G01B 9/02063* (2013.01); *G01B 9/02091* (2013.01)

(58) Field of Classification Search
CPC ............ G01B 9/02063; G01B 9/02058; G01B 9/02004; G01B 9/02091; A61B 3/102
USPC ......................................... 351/200, 205, 206
See application file for complete search history.

(56) References Cited

U.S. PATENT DOCUMENTS

| | | | | |
|---|---|---|---|---|
| 5,994,690 A | * | 11/1999 | Kulkarni | A61B 5/7257 250/216 |
| 8,836,953 B2 | * | 9/2014 | Johnson | G01B 9/02004 356/450 |
| 2009/0086213 A1 | * | 4/2009 | Masuda | A61B 5/0066 356/479 |
| 2014/0028997 A1 | * | 1/2014 | Cable | G01B 9/02091 356/51 |
| 2014/0160488 A1 | * | 6/2014 | Zhou | G01B 9/02004 356/479 |

\* cited by examiner

*Primary Examiner* — Tuyen Tra

(57) ABSTRACT

En face views of OCT volumes provide important and complementing visualizations of the retina and optic nerve head investigating biomarkers of diseases affecting the retina. We demonstrate the combination of real time processing of OCT volumetric data for axial tracking. In combination with a Controllable Optical Element (COE), this invention demonstrates acquisition, real time tracking, automated focus on depth resolved en face layers extracted from a volume, and focus stacked OCT volumes with high resolution throughout an extended depth range.

20 Claims, 9 Drawing Sheets

Scale bars denote 200 μm.

SYSTEM AND METHOD FOR DYNAMIC FOCUS CONTROL

CROSS REFERENCE TO RELATED APPLICATIONS

The instant application is a utility application and claims priority to the U.S. provisional patent application 62/292,361 titled "Retinal Optical Coherence Tomography at 1 um with dynamic focus control and axial motion tracking.", filed on 7 Feb. 2016. The entire disclosure of the Provisional U.S. patent Application no. 62/292,361 is hereby incorporated by this reference in its entirety for all of its teachings. This benefit is claimed under 35. U.S.C. $ 119.

FIELD OF TECHNOLOGY

The following description relates to a method and a system for imaging and tracking the position of a moving specimen on the subsurface with high optical resolution. More specifically the description is relevant to imaging of biological specimen such as a retina using a form of low coherence interferometry such as optical coherence tomography (OCT) and optical coherence domain reflectometry (OCDR), wherein high resolution is obtained relative to the maximum permitted by the pupil of the eye.

BACKGROUND

Optical coherence tomography (OCT) provides cross-sectional images of the retina with exquisite axial resolution, and is commonly used in ophthalmology. High resolution OCT retinal imaging is important to non-invasively visualize the various retinal structures to aid in better understanding of the pathogenesis of vision-robbing diseases. In OCT, the axial resolution is determined by the optical spectrum of the light source, whereas the lateral resolution is determined by the numerical aperture (NA) of the light delivery optics and the sample. Conventional OCT systems have a trade-off between lateral resolution and depth-of-focus. Clinical OCT systems operating at the 830 nm or 1060 nm center wavelength regions commonly use a beam diameter of ~1 mm at the cornea, corresponding to a lateral resolution on the order of ~20 µm at the retina. This resolution is approximately one order of magnitude worse than the theoretical best axial OCT resolution, which is on the order of ~2 µm. By increasing the probe beam diameter at the cornea, the lateral resolution can be improved, but this approach reduces the depth-of-focus as a trade-off.

For retinal OCT imaging, the cornea and lens act as the imaging objective, so the beam diameter at the pupil determines the numerical aperture and hence the focused spot size at the retina. Since imaging through the entire thickness of the retina and structures of the optic nerve head (ONH) is desirable, conventional retinal OCT configurations have a lateral resolution that is less than what is achievable based on the limiting pupil of the eye. Therefore, an extended depth-of-focus imaging system capable of maintaining high lateral resolution within the layers of interest is important. Methods have been proposed to overcome this axial depth limitation when imaging with high resolution. These methods include mechanical motion of the sample arm, the addition of focus-modulating elements, such as acousto-optic tunable lenses and Axicon lenses, and adaptive optics. Multi-beam systems have also been reported. Computational approaches such as interferometric synthetic aperture microscopy (ISAM) have also been used to correct for defocus in post-processing and provide axial focus extension.

SUMMARY

The invention discloses a system and method for depth resolved axial retinal tracking and automatic focus optimization for high resolution imaging over a deep range and for extended-focal-range OCT. In one embodiment, a Controllable Optical Element (COE) is incorporated into the light delivery optics of the OCT system at a position in the optical path that is optically conjugated to the pupil of the eye enabling motionless focus adjustment for high resolution and wide field imaging. Optical conjugation means that the wavefront is optically relayed from the COE to the pupil of the eye; one embodiment of an optical relay is a 4-f telescope constructed from two lenses, wherein the COE is located at a focal length away from the first lens, the lenses are separated by the sum of their focal lengths, and the pupil of the eye is located at a focal distance away from the second lens. In an embodiment of this invention, the images of the retina acquired by OCT are tracked in axial position in near real time based on features in the volumetric data. Regions Of Interest (ROI) relative to the tracking features may be automatically or manually selected for focus optimization.

In an embodiment, the focus optimization is performed automatically by adjusting the optical power of the COE and calculating an image quality metric based on a depth resolved image plane (referred to as an 'en face' image or as a C-scan image) from the volume data. After optimization, the COE may be used to acquire multiple volumes focused at different depths. These volumes are subsequently registered and stitched together to yield a single, high resolution focus stacked dataset over an extended axial depth. Using this method and system, we show high resolution images of the retina and optic nerve head, from which we extracted clinically relevant parameters such as the nerve fibre layer thickness, lamina cribrosa microarchitecture, and the cone photoreceptor mosaic outside of the parafovea. The high resolution visualization of the retinal morphology acquired in this manner can assist ophthalmologists to better understand the pathogenesis of retinal diseases or monitor the effects of treatments.

BRIEF DESCRIPTION OF THE DRAWINGS

FIG. 2D was generated by stitching together FIG. 2A to FIG. 2C, and FIG. 2E is an en face image generated from the same dataset.

FIG. 2F is a cross sectional image of a macula acquired with the same imaging system.

In FIG. 4A the OCT system operator manually selects the thickness of ROI (410) and two A-scans for segmentation (420).

In FIG. 4B the algorithm detects the maximum-intensity pixel at each location (430).

In FIG. 4C the locations of the brightest layer in the retina A-scans are interpolated from the two maximum-intensity pixels (430). These locations are used to track the axial position of the retina, and also used to determine the tilt of the en face layer (450).

In FIG. 4D the en face image is generated by summing up the pixels within the selected depth range (460). The image is acquired at an eccentricity of ~6° from the fovea. Scale bars denote 50 µm.

FIG. 7A is a cross-sectional B-scan image.

FIG. 7B is an en face image with the focus at the nerve fibre layer (NFL) while tracking the position of the outer retina.

FIG. 7C is an en face image with the focus at the outer plexiform layer (OPL) while tracking the position of the outer retina.

DETAILED DESCRIPTION

This invention describes a novel, axial tracking, automated focus, high speed OCT imaging system and method for acquiring in vivo high resolution images of the entire retinal structure and optic nerve head using a focus stacking method. Since recent developments in OCT engines using Fourier Domain (FD) detection have resulted in longer imaging depths with high Signal-to-Noise Ratio (SNR), the entire thickness of the retina can be visualized even with a high numerical aperture sample arm. However, high lateral resolution imaging is limited to the depth-of-focus. Furthermore, imaging the retina with a tightly focused spot reduces the intensity in the regions outside the focal depth because of the larger beam diameter, resulting in lower resolution and lower SNR. Hence, methods are required for focusing on specific depth resolved layers in the sample, and for acquiring volumetric data with high lateral resolution over an extended depth-of-focus.

Figure 1A:
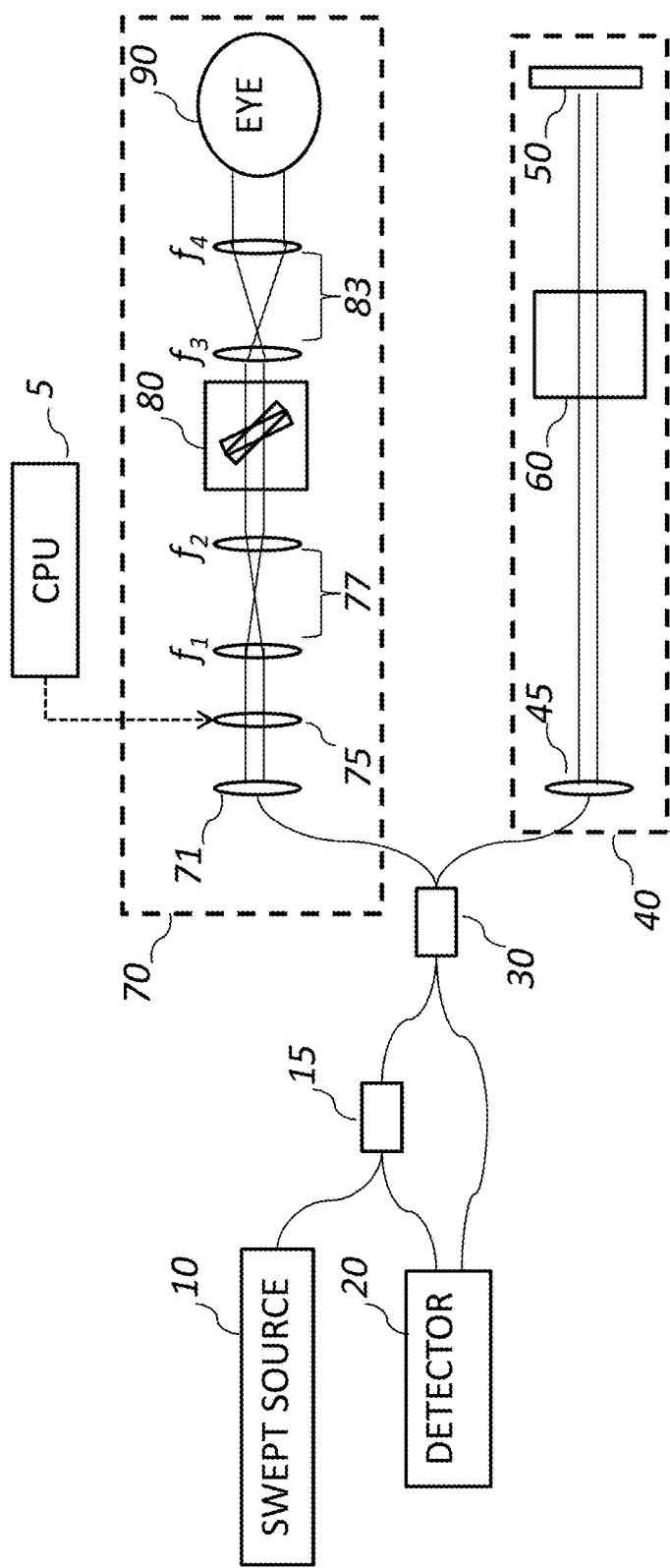
FIG. 1A shows a schematic representation of the OCT system, which is an embodiment of the invention.

An embodiment of the invention is schematically represented in FIG. 1A. In the demonstrated configuration, the OCT engine is based on a wavelength swept laser (or light source) (10), in a configuration known as Swept Source (SS) OCT or alternatively as Optical Frequency Domain Imaging (OFDI). The detector is a balanced photodiode (20). An unbalanced photodiode could also be used. The OCT system is computer controlled, combining and providing signals for timing and control, and for processing the interferometric data into images or volumetric data. It could be controlled using an embedded controller as well. The fibre coupler (30) splits the light from the source into reference (40) and sample (70) paths or arms. The fibre coupler may have a splitting ratio of 50/50, or some other ratio. In some embodiments, the fibre coupler (or fibre optic beam splitter) is replaced by a free-space beam splitter. The reference arm has a mirror (50) typically mounted on a translation stage and may contain dispersion compensating optical elements (60). In an alternate embodiment, the reference arm could be a fibre with a fibre-integrated mirror. The sample arm optics (70) are designed for high resolution imaging of a retina, and the final objective is the cornea and intraocular lens of the eye (90). A scanning mechanism (80) is used to scan the angle of light incident on the cornea, which in turn scans the lateral position of the focused spot on the retina. The light returning from the sample and reference arms are combined through the beam splitter to create an interference signal and directed towards the detector (20). The optical interference signal is processed to construct depth resolved images of the sample. The processing of the acquired signal is coordinated with the control of the scanning mechanism in the sample arm and can be used to generate three dimensional (3D) volumetric data of the sample. In some embodiments, the sample could be a human or animal eye.

Alternative variations of this configuration could replace the SS OCT with a Spectral Domain/Spectrometer Domain (SD) OCT or a Time Domain (TD) OCT. For Spectral Domain OCT, the swept laser is replaced by a broad band light source, and the detector is spectrally resolved, for example, using a spectrometer. For Time Domain OCT, the swept laser is replaced by a broad band light source, and the reference mirror position is scanned axially (or angularly) to generate interference fringes. Thus, TD-OCT comprises of a scanning reference mirror. Operating wavelengths for retinal imaging are from the visible to near infrared. In one embodiment, the central wavelength is 1060 nm, with a bandwidth of ~70 nm. In another embodiment, the central wavelength is 840 nm, with a bandwidth of ~50 nm. Other embodiments may use combinations of central wavelength ranging from 400 nm to 1300 nm, and bandwidth of approximately 5 nm up to over 100 nm, and in some cases with central wavelengths around 700 nm and bandwidths of several 100's of nanometers. In some embodiments the fibre coupler (15) is an optical circulator. In other embodiments of the system, the detection may not be balanced, and fibre coupler (15) may be replaced by a direct optical path from the source to the interferometer fibre coupler (30). Alternative variations of the interferometer configuration could be used without changing the imaging function of the OCT engine.

Figure 1B:
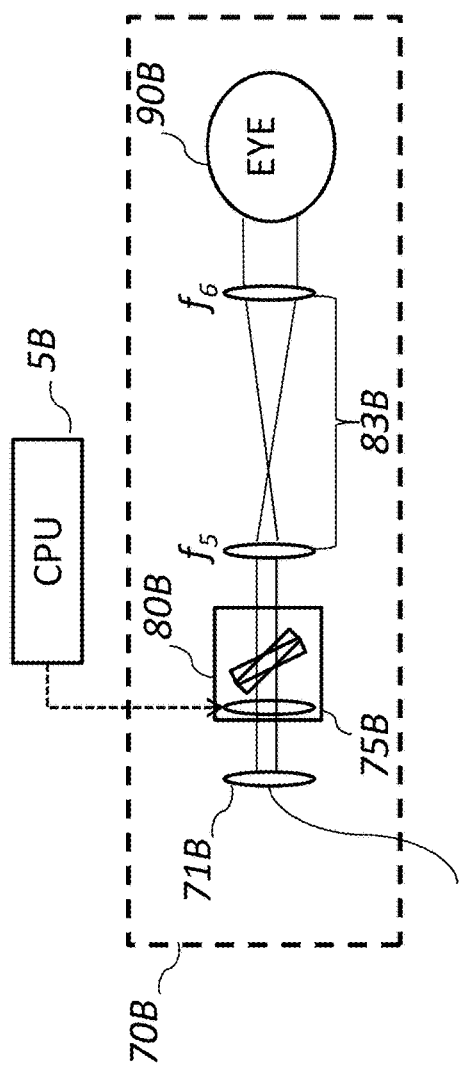
FIG. 1B shows another embodiment of the sample arm only that is more compact and with fewer optical elements.

An embodiment of the sample arm optics for high resolution retinal imaging (70) is schematically illustrated in FIG. 1A. Light from the fibre is collimated (71) and directed to a Controllable Optical Element (COE) (75). The COE is optically relayed to be approximately optically conjugated to the galvanometer mounted scanning mirrors (80) and the pupil of the eye (90). In this embodiment, two sets of the relay optics (77) and (83) are placed between the COE and ocular pupil, optically conjugating the wavefront at the COE, the scanning mirror pair (80) and the pupil of the eye. The relay optics (77) and (83) thus convey the dynamically changing optical power of the COE to the pupil of the sample. An alternative configuration, schematically presented in FIG. 1B, would have the COE and scanning mirrors clustered close together (80B), having each of them approximately conjugated to the pupil by the optical relay lenses (83B). The size of the optical beam at the pupil of the eye is determined by the selection of lenses for the fibre collimator and the optical relays. In one embodiment, the focal length of the collimator is 7.5 mm, and the focal lengths of the lenses in the optical relays $f_1$, $f_2$, $f_3$, $f_4$, $f_5$, $f_6$ are in the range of approximately 10 mm to 1000 mm in order to deliver a beam size at the pupil of 3 mm. Lenses with other diopter ranges providing different beam sizes at the pupil could be used without limitation. Positioning the COE in conjugation with the optical pupil plane allows adjusting the focus without moving any optical element in the system, it also ensures the imaging beam is pivoting angularly at the entrance pupil and minimizes the lateral displacement on the pupil while the imaging beam is being scanned and the focus is being adjusted, which consequently enables the high resolution and wide field of view imaging.

In one embodiment, the COE is a variable-focus liquid lens (VL; ARCTIC 316-AR850, Lyon, France). The variable-focus lens typically has a dynamic range of 18 diopters (−5 D to +13 D); lenses with other diopter ranges could be used without limitation. Other suitable types of COE such as a liquid crystal spatial light modulator, deformable mirror, or other controllable optical elements, capable of generating phase profiles corresponding to different amounts of defocus, could be used. In some embodiments, a COE that can generate phase profiles including, but not limited to, one or more of defocus, astigmatism, or other aberrations of the eye. In other embodiments, additional sets of relay lenses can be used to incorporate more than one COE, and/or more than one type of COE, at optical planes that are conjugated to the scanners and the pupil of the eye. Thus in some embodiments, the controllable optical element (COE) is optically relayed to be (in some other embodiment, approximately) optically conjugated to a scanning element and a pupil of the eye.

In some embodiments, the galvanometer mounted mirrors in the light delivery optics could be replaced by a MEMS (micro-electro-mechanical systems) or MOMS (micro-opto-mechanical-systems) or MOEMS (micro-opto-electro-mechanical systems) scanning mirror(s), or acousto-optic or electro-optic beam deflecting elements to scan the incident angle of the beam at the cornea, which corresponds to a scanning in the lateral position on the surface of the retina. In another embodiment, a resonant mirror (or resonant mirrors), or a crystalline beam deflector (or crystalline beam deflectors) could be used for scanning. In other embodiments, any combination of scanning elements may be used.

At each scan position, corresponding to a point on the retina, the OCT signal acquired at the detector is generated from the interference of light returning from the sample and the reference arms. In some embodiments, a reference reflection may also be incorporated into the sample arm. Such a configuration is called a common-path-interferometer.

The interference signal is processed to generate a depth profile of the sample at that position on the retina, called an A-scan. A cross-sectional B-scan image is generated by controlling the scanning of the position of the beam laterally across the retina and acquiring a plurality of A-scans; hence a two dimensional (2D) B-scan depicts the axial depth in the sample along one dimension, and the lateral position on the sample in the other dimension. FIGS. 2A-2F show representative B-scans of a retina in the optic nerve head region (FIG. 2A-2E) and in the macular region (FIG. 2F) acquired using an embodiment of the present invention. A collection of B-scans acquired at different locations on the retina constitute a volume. In one embodiment, the B-scans are acquired at different elevations. In another embodiment, the B-scans are acquired in a radially spoked pattern. In other embodiments, the B-scans are acquired in a spiral, or Lissajous, or other patterns. The volumetric data are assembled by the processor, which may be a computer or an embedded processor, or a Graphics Processing Unit (GPU) or a Field-Programmable-Gated-Array (FPGA) or a combination of one or more of these processors. A depth layer extracted from a volume is called an en face image, or alternatively in some embodiments, a C-scan.

In one embodiment, an instrument control sub-system controls the acquisition of the interference signal; and the instrument control sub-system may also configure at least one controllable optical element to adjust the focus within the sample. The instrument control sub-system may also construct depth resolved images (i.e., B-scans) and three dimensional data sets (or volumetric datasets) of the sample by processing the optical interference signal.

The instrument control sub-system may further comprise of at least one processor configured to provide timing and control signals; at least one processor for converting the optical interference to the 1 or 2 or 3-dimensional data sets. The processor(s) may extract a specific depth layer image (or en-face image) within the three dimensional data sets; and calculate a merit value from the extracted depth layer image within the sample.

In one embodiment a Graphics Processing Unit (GPU) could be used for real time processing of the B-scan image data. For example, a GPU-accelerated FD-OCT acquisition code was utilized for this demonstration with a GeForce GTX Titan (NVIDIA Santa Clara, Calif.) that provided a 1024-pt A-scan processing rate of 4 MHz, which is significantly faster than the data acquisition rate (200 kHz), and thus permitting computational bandwidth for additional processing. In other implementations, the OCT signal processing could be performed by a Central Processing Unit. In other implementations, a Field Programmable Gate Array (FPGA), Application Specific Integrated Circuit (ASIC), or other Digital Signal Processing (DSP) chip or hardware or software may be used. In another configuration, a combination of any of these processing architectures may be used.

Focus optimization with high resolution OCT is performed on a depth resolved layer of the retinal volume data with the tracking of the axial sample motion. During retinal OCT imaging, the subject is usually supported by a forehead and chin rest for stabilization. However, the axial retinal motion remains present in most cases. An aspect of this system and method is tracking the axial location of the retina in order to extract a depth resolved en face image with correspondence to a physiological retinal layer. The real time image-based axial tracking and layer segmentation also allows the optimization to be fine-tuned to focus on specific physiological retinal layers instead of optimizing for the brightness along the entire retinal thickness. This is particularly important for the case of high resolution OCT, in which the depth-of-focus is shorter than the axial imaging depth.

Figure 3:
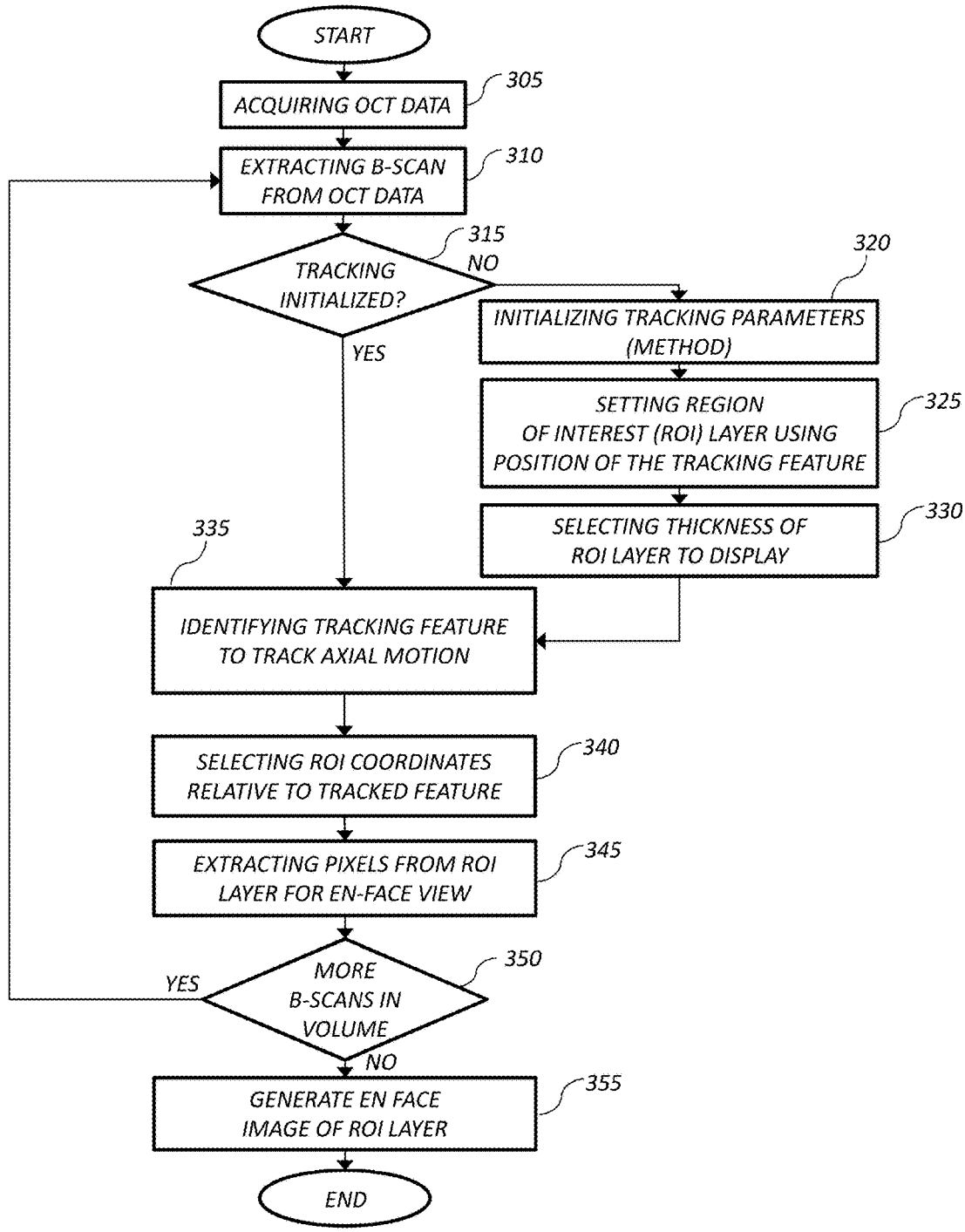
FIG. 3 is a flow chart of a method tracking the sample based on depth resolved features. This is an embodiment of this invention.

The method by which the depth resolved tracking and extraction of an en face image from the OCT volume is described by a high level flow chart in FIG. 3. The processing is performed on the B-scan images in real time as the data are acquired in order to minimize lag between the time that the images are acquired and when the processed results are available for tracking, calculation of image quality metrics, or display. Tracking the axial position of the retina permits visualization of en face retinal images with meaningful correspondence to the cellular layer physiology during acquisition even in the presence of sample motion. In one embodiment of the invention in the application of retinal imaging, the position of the photoreceptor layer within the outer layer of the retina could be tracked. In another embodiment, the position of the nerve fibre layer at the retina/vitreous humor interface could be tracked. In another embodiment, multiple layers could be segmented and tracked, or tracking could be performed by registration of images in subsequent B-scans.

FIG. 3 represents a high level flow chart for one embodiment of the method that tracks the movement of the retina. The illustrated method starts at Step 305, acquiring OCT data, and then Step 310, which is the extraction of a B-scan from the OCT acquisition. In Step 320, the feature in the B-scan to be tracked is identified and delineated. In Step 325, the position of the Region Of Interest (ROI) in the B-scan relative to the tracked layer is selected, and in Step 330, the axial extent of the ROI with respect to the tracked feature is determined. In Step 335, the tracking is performed on the B-scan. In Step 340, the ROI is selected from the B-scan using the coordinates determined relative to the tracked feature. In Step 345, the ROI is extracted and the axial information is projected into a line indexed to the final position of the en face image corresponding to the B-scan location. The projection of the ROI onto the line may be performed by axial summation of the pixels in each A-scan of the ROI, or by maximum intensity projection, or other method. At Step 350, the process is repeated for a plurality of B-scans. Once all the B-scans in the volume have been collected and processed, at Step 355 the final depth resolved en face image is assembled from each of the line projections indexed to the position of the B-scan and the process terminates.

In one embodiment, the brightest layer in an OCT macular scan of the retina is tracked (Step 325). In another embodiment, features from the outer retina could be used.

Figure 4D:
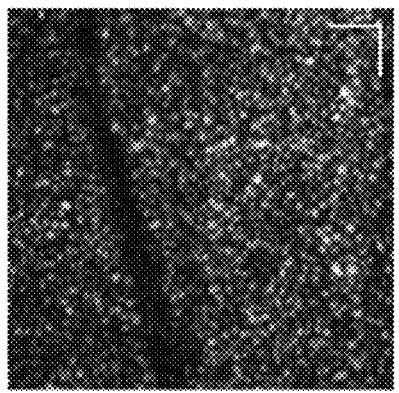
FIGS. 4A-4D illustrate representative steps of a simple segmentation algorithm for real time axial tracking and en face visualization.
Figure 4C:
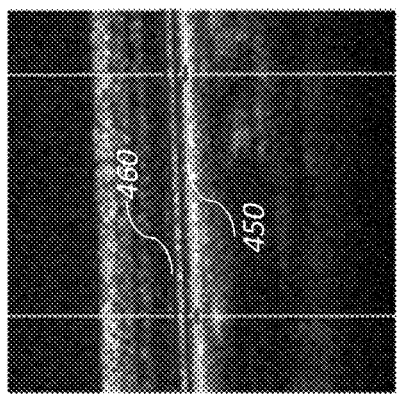
Figure 4B:
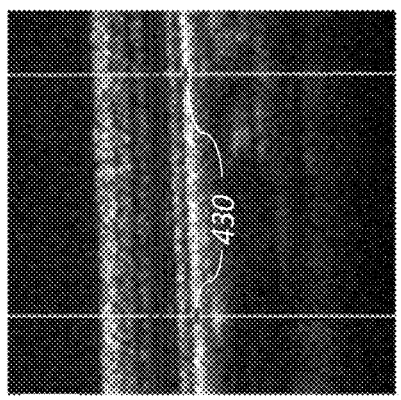
Figure 4A:
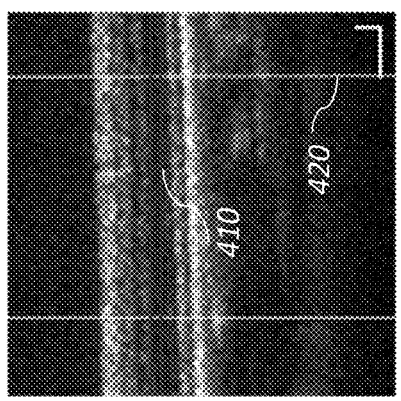

In one embodiment of the method (described in FIG. 3), the OCT system operator selects the thickness of the en face layer of interest as (410), as well as two lateral A-scan positions on the retina as indicated by (420) to be used for tracking, as indicated in FIG. 4A. At each of the selected A-scan positions, the pixel with the maximum intensity (430) is identified, and the coordinates are used to determine the degree of retinal tilt (if present) as shown in FIGS. 4B and 4C. This process may be performed for any number of A-scans across the B-scan image. The points tracked at the A-scan positions in the B-scan image may be joined by a straight line (450), or in other embodiments by a piecewise connected line segments, or a curved line. This line represents the tracked feature of the retina. This process is repeated for each B-scan in the volume. The location of this feature is thus captured in the presence of axial motion between the B-scans, and also in the case of the features that are tilted in the image plane with respect to the plane orthogonal to the incident beam of light. A Region Of Interest (ROI) layer is defined by an axial offset relative to the tracked line. The thickness of the ROI in pixels is also determined. An en face image is constructed by assembling the points from the ROI in each B-scan image via summation or maximum intensity projection or other means of the values in an A-scan. The en face projection of each B-scan is assembled into an en face image as indicated in FIG. 4D which is an image of the photoreceptor layer. This layer is a depth resolved en face image of the OCT volume. In other embodiments, pixels in the axial direction may be summed or maximum projected onto the line representing that B-scan in the en face image. In other embodiments, the en face layer may be generated from a region of the retina that is offset from the layer that is tracked. For example, a fixed offset may be generated from the tracked line in order to extract an en face image of the capillary network in the outer plexiform layer. The offset from the tracked layer and the axial thickness of the pixels used to generate the en face image may all be selectable by the OCT system operator.

In other implementations of the depth resolved OCT tracking, the top retinal layer may be tracked, or the bottom layer may be tracked. In another embodiment, any layer including an intermediate layer may be identified for tracking by incorporating edge detection algorithms or more sophisticated segmentation algorithms to analyze the retinal B-scan image data. In other implementations, multiple points along the B-scan may be used for feature identification and tracking, providing a piecewise straight or curved line segmentation of the retina. The alternative embodiments of the layer segmentation may be particular beneficial in cases where edema, drusen, intra- or sub-retinal fluid or other pathology distort the shape of retina. Another embodiment is to register subsequent B-scans to the first B-scan, but this may only work in cases where there is sufficient similarity in the images across the volume. In one embodiment of this method, the real time processing is implemented on a GPU. In other embodiments of this method, the real time processing may be done on a Central Processing Unit (CPU), Field Programmable Gate Array (FPGA), Application Specific Integrated Circuit (ASIC), Digital Signal Processing (DSP) chip, or any combination of the above.

Figure 5B:
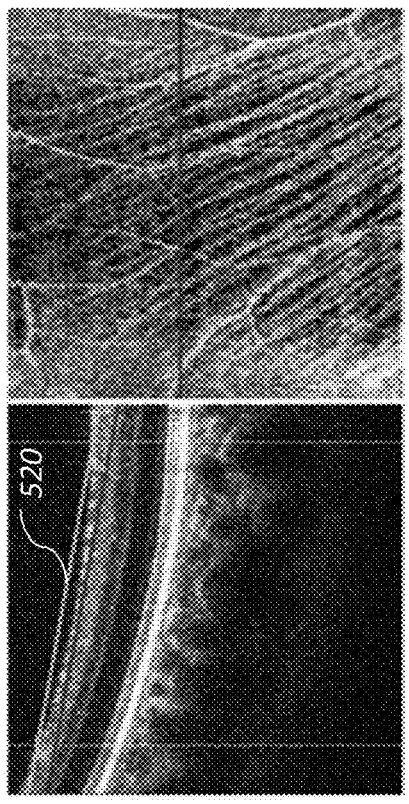
FIG. 5B shows images with tracking of the retinal nerve fibre layer acquired using an embodiment of the present invention. With the segmentation of the ROI, the retinal tilt and axial motion is accounted for, and the nerve fibre layer en face image (on the right) extracted from the segmented depth range (520) corresponds to the nerve fibre layer on the OCT B-scan on the left. Scale bar denotes 250 µm.
Figure 5A:
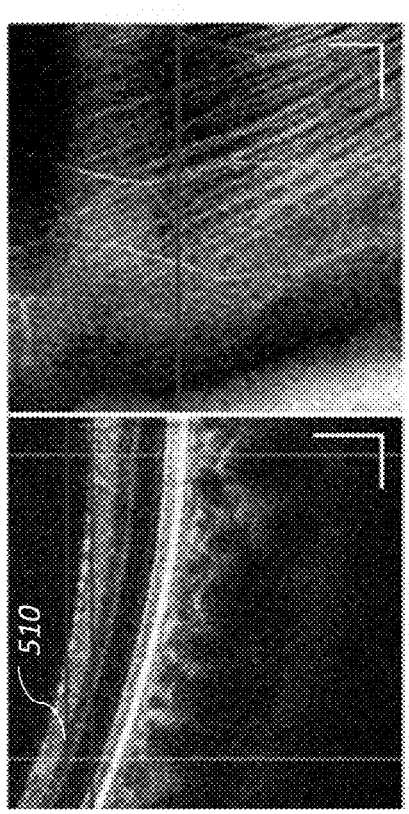
FIG. 5A shows a representative en face image (on the right) extracted from a certain depth section (510) within the image range acquired without segmentation of the retinal layers in the B-scan (on the left), the resultant en face image is not from a single retinal layer, but is instead a contribution of multiple retinal layers.

The importance of tracking and extracting a physiologically relevant depth resolved en face image from an OCT volume is presented in FIGS. 5A and 5B. In the embodiment of this invention used to acquire the images in FIG. 5A-5B, the outer retina was tracked at two lateral A-scan locations, and an offset was manually applied corresponding to the thickness of the retina in order to extract the nerve fibre layer. In the en face image generated from the segmented B-scans, the nerve fibre bundles are clearly visualized FIG. 5B). In comparison, without segmentation, artifacts from the retinal tilt and axial motion degrade the en face image, and the resultant en face view is not from a single retinal layer, but is instead a contribution from multiple retinal layers FIG. 5A).

Figure 6:
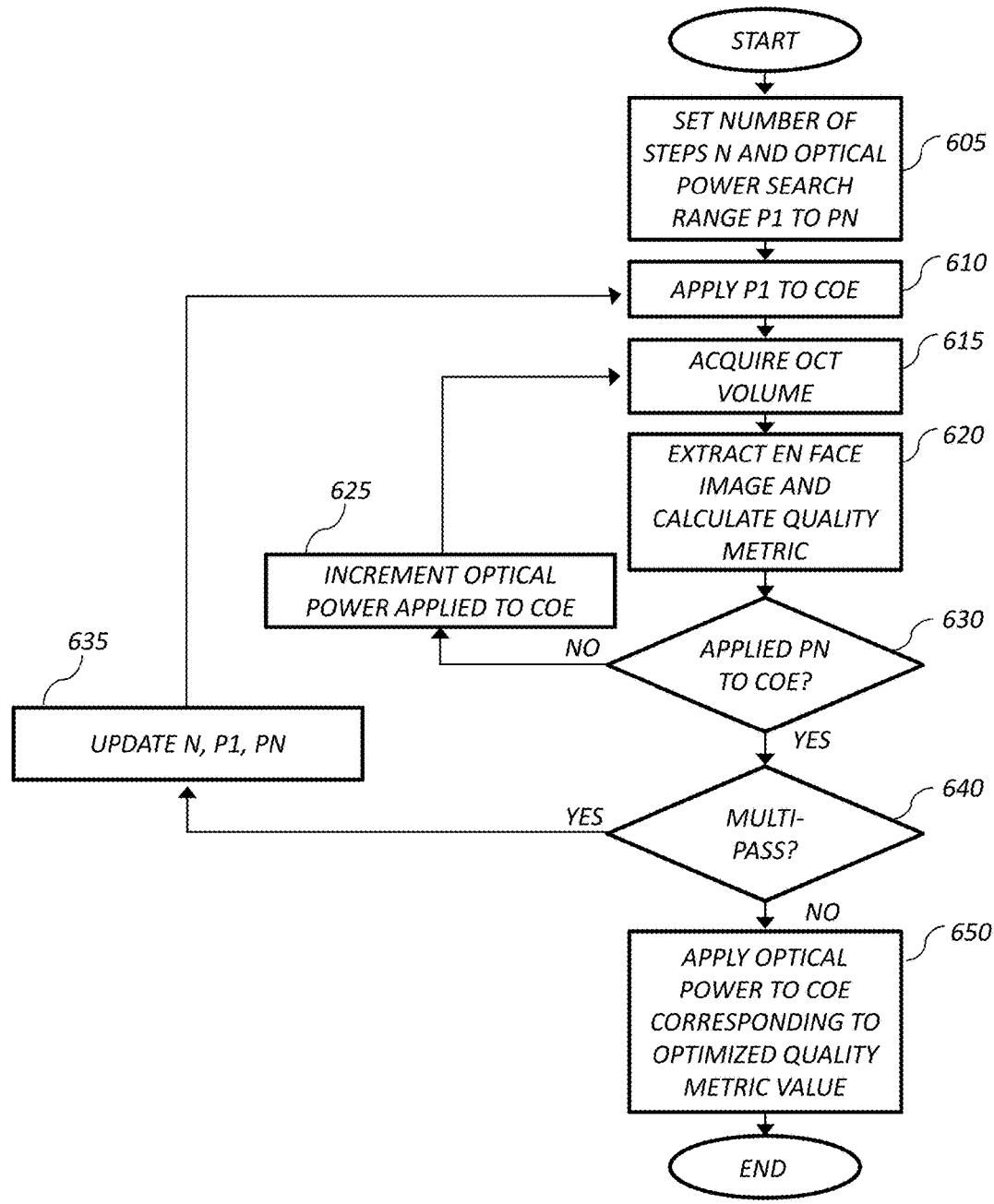
FIG. 6 is a high level flow chart (according to an embodiment of the invention) of a focus optimization method on a depth resolved en face image extracted from the OCT volume.

A high level flow chart of the method for optimizing the focus on the depth resolved en face images is in FIG. 6. The method starts at Step 605 by setting parameters for the starting optical power and the final optical power applied to the COE, viz., P1 and PN, respectively, and the number N steps to be searched in that range, as well as the number of optimization passes. At Step 610 the COE is initialized to a starting optical power P1. At Step 615, an OCT volume is acquired, and at Step 620 the method described in FIG. 3 is used to generate a depth resolved axially tracked en face image. Also at Step 620 the image quality metric is computed based on the extracted image. If the optical power applied to the COE is not PN, the optical power of the COE is incremented at Step 625 and the process is repeated. If the value of PN is applied to the COE, the current optimization pass ends. At Step 640, if this is a multi-pass optimization, then the parameters N, P1, and PN are updated based on the plurality of merit values from the current pass. If the final iteration of the multi-pass optimization has been reached, Step 650 selects the optimized value from the collection of the plurality of merit values and the corresponding optical power is applied to the COE.

The focus optimization operates on a plurality of OCT volumes, and is performed in near real time in combination with image acquisition and processing. The automated focus optimization method is driven by an image based metric calculated on the depth resolved and tracked en face image extracted from each of the volumetric OCT data sets. In one embodiment, the image quality metric is the brightness of the selected depth resolved en face layer, calculated as the sum of the intensity at each pixel, maximum intensity, or thresholded intensity. In other embodiments, sharpness metrics may be used, or image features (for example accentuated through an edge filter) may be used. In other embodiments, the image quality may be evaluated on the image itself, or in a transform domain (e.g., the Fourier transform) or any other representation of images described by a basis functions-set. In other embodiments, the metric may be based on reflection characteristics, image gradient or entropy of the image. Image gradient maybe computed using a differential operator or a gradient filter. Entropy is indication of the amount of information present in an image. It may be calculated as the sum of $P_i \log(P_i)$ (where $P_i$ is the probability that the difference between two adjacent pixels is "i"). The summation is performed over the possible range of pixel intensities (or brightness) "i". There may be other methods of computing image gradient and entropy.

One embodiment of the focus optimization method operates on the quality of the en face image as the optical power of the COE is changed. Following the flow chart presented in FIG. 6, with the COE initialized at a 'low' optical power (i.e. P1), a depth resolved and tracked en face image is acquired and extracted from the OCT volume; the image quality merit value is calculated on this en face image. The optical power of the COE is then incremented, and a subsequent OCT volume is acquired and image quality metric is calculated from the en face image extracted from the same depth resolved and tracked retinal layer. This process is repeated until reaching the 'high' optical power limit of the search range (i.e. PN). In one embodiment, the number of increments may be 20 within a 5 Diopter (D) range. Other increment values and binning could be used without limitation. After completing the search, the value of the optical power that corresponded to the optimized image quality metric would then be applied to the COE, corresponding to the best focus. Another embodiment of the method would use a multi-pass approach, starting with a large search range, and then fine-tuning the search range in successive passes. In one embodiment, the first pass of the optimization method applies 7 different ocular diopter values within a 5-7 D range and records the resultant brightness at the specified tracked and depth resolved retinal layer as the merit value. In the subsequent passes of this embodiment, the algorithm tests a narrower range around the diopter value that gives the maximum intensity in the previous pass. In one embodiment OCT volumes comprising of 10 B-scans/volume are acquired for each diopter shift and used to calculate the summed intensity within the selected en face region. In this embodiment, the optimization rate is 25 Hz per step, and the entire optimization process is completed in ~1 second. In other implementations, the focus optimization time could be reduced to avoid accommodation of the eye. Other values of B-scans/volume and optimization rates could be used without limitation.

Figure 7A:
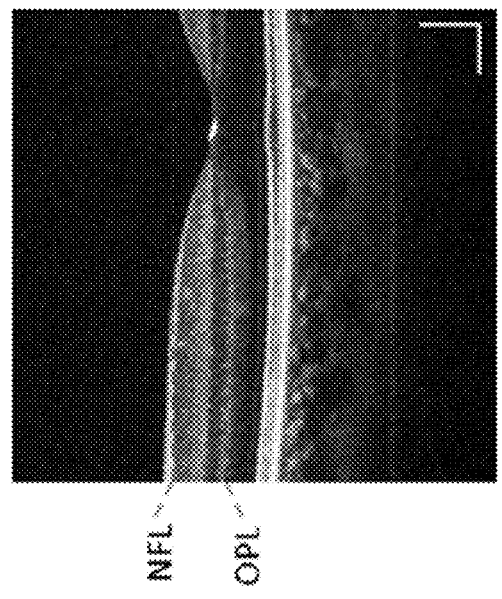
FIGS. 7A-7C illustrate representative images of high resolution OCT with the focus optimized on different layers.
Figure 7B:
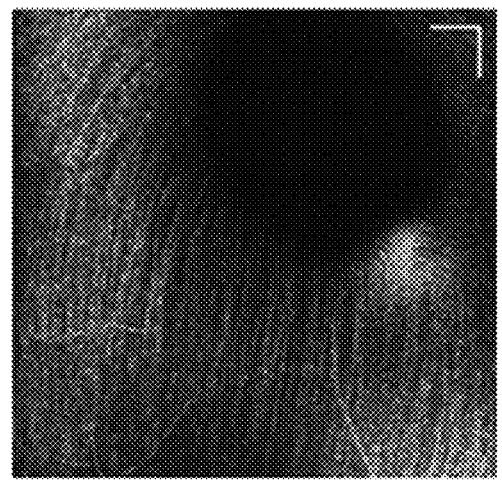
Figure 7C:
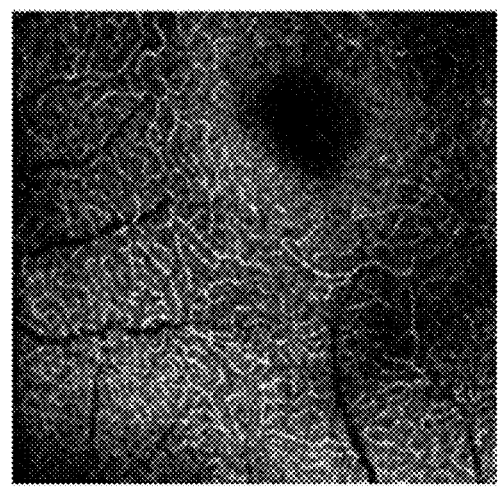

Representative images demonstrating the results of the depth resolved tracking and automated focusing on a physiological layer in OCT retinal data are presented in FIGS. 7A-7C. The B-scan image in FIG. 7A shows the bright layer in the outer retina that was used for segmentation and tracking and the depth regions that were extracted for automatic focusing. FIG. 7B shows the image results after automated tracking and focus optimization on the nerve fibre layer (NFL), and FIG. 7C shows the image results after automated tracking and focus optimization on the capillaries of the outer plexiform layer (OPL). The high resolution of the system permitted visualization of the nerve fibre bundles in the retinal nerve fibre layer, and the capillary network of the outer plexiform layer with high contrast.

Figure 8:
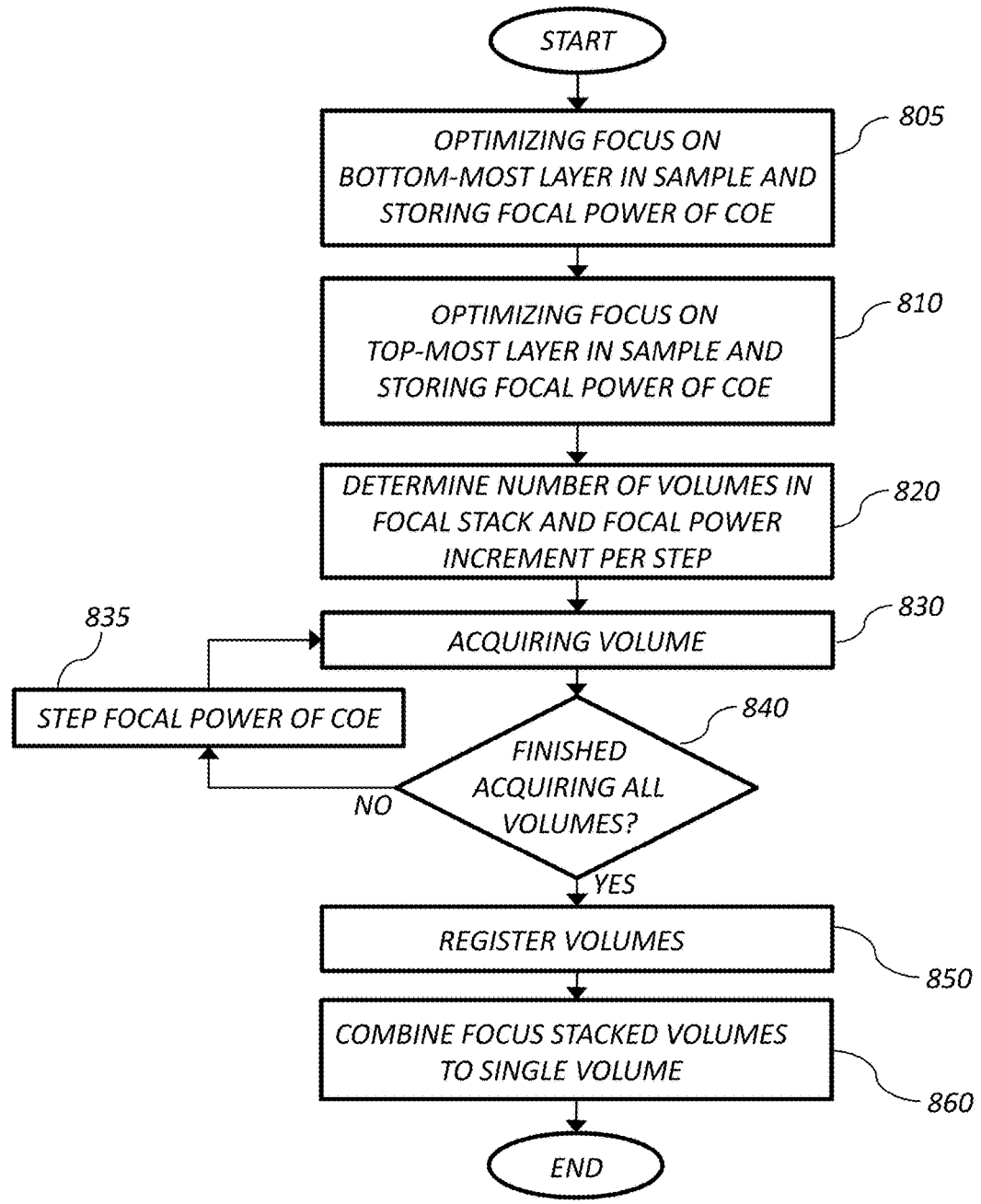
FIG. 8 is a flow chart (according to an embodiment of the invention) of focal stacking for the acquisition of a high lateral resolution volume over an extended depth-of-focus.

Retinal structures that are significantly larger than the depth-of-focus of the high resolution imaging system can be acquired using focus stacking. A high level flow chart of focal stacking is presented in FIG. 8. The method starts at Step 805, with an automatic focus optimization performed at the bottom-most layer of the retina to be acquired, for example the lamina cribrosa, and the optical power applied to the COE is recorded. In Step 810, an automated focus optimization is performed for the top-most feature in the retina to be acquired, for example the retinal nerve fibre layer, and the optical power applied to the COE is recorded. In Step 820 the number of stacked volumes is determined based on the extent of the retinal structure and the depth-of-focus of the high resolution imaging beam. In one embodiment, in Steps 830, 835, and 840 a set of 3-5 volumes are acquired as the optical power applied to the COE is stepped through the range determined in Steps 805 and 810. More or less volume sets could be acquired as the focus value is stepped through more or less steps, respectively. In Step 850, the volumes are registered, and then blended together to form an extended depth high resolution volume in Step 860.

During the acquisition of the sequential volumes, motion artifact is likely to occur that will cause the structures in the focus stack volumes to mismatch. In order to compensate for the mismatches, motion correction is performed in post-processing after completing the multi-volume acquisition. In one embodiment, the relative translation between B-scans is assessed using phase correlation, and B-scan to B-scan motion registration is performed. After the 2D motion registration, volumetric registration may be performed using the 3D rigid registration toolbox in Amira (FEI, OR), followed by 3D non-rigid registration using the Medical Image Registration Toolbox (MIRT). Other software libraries could be used. For the 3D registration, each volume in the focus stacked dataset is registered to the previously acquired volume to maximize the amount of information overlap during the registration. After the volume registration, in one embodiment, the A-scans within each volume are summed to determine the position of the best focus within the volume, since the depth at which the volume is focused will have greater intensity than the out-of-focus regions. From the comparison of the A-scans, the peak intensity locations are approximated so that the separations between the peaks are evenly spaced. In one embodiment, a set of Gaussian masks was automatically generated at the approximated focus locations and normalized to perform weighted averaging, which results in a high resolution volume of the entire axial extent of the optic nerve head as visible with the OCT system.

Figure 2A:
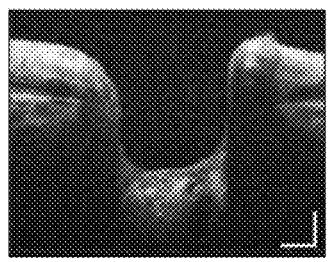
FIGS. 2A-2F show representative images of the retina (macula and optic nerve head) acquired with an embodiment of the invention. The focal depth is shorter than the image depth. This is particularly pronounced in the optic nerve head cross-sectional images in FIGS. 2A-2C.
Figure 2B:
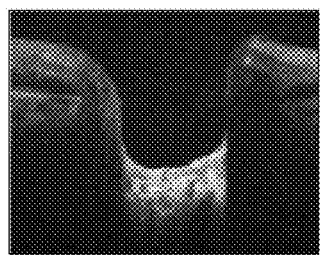
Figure 2C:
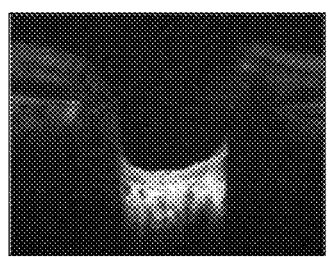
Figure 2D:
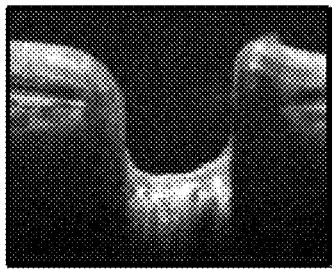
Figure 2E:
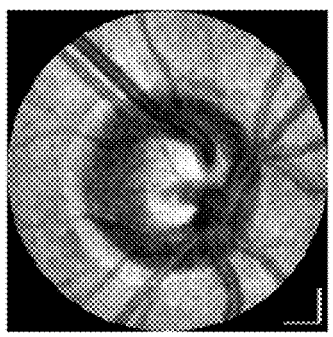
Figure 2F:
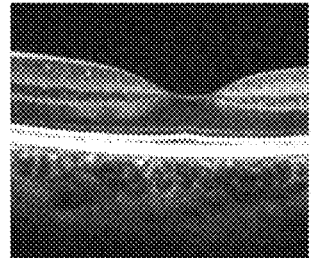

The results of the focus stacking method are shown in FIGS. 2A-2E for a representative data set acquired at the optic nerve head. In the representative B-scan OCT images shown in FIG. 2A-FIG. 2C, focus was set at: FIG. 2A the retinal surface, FIG. 2B the bottom of the cup, and FIG. 2C the lamina cribrosa. At these different focal positions, the top, middle, or bottom of the optic nerve head can be seen to be brighter relative to the other image regions. FIG. 2D is the stitched result of three different focus stacked B-scans and FIG. 2E is summed voxel projection of the entire focus stacked dataset.

In the demonstrated embodiment of the invention the diameter of the imaging beam at the eye's pupil was ~3 mm. Other diameters could be used without limitation. With this imaging beam diameter, the dominant aberrations in a normal population of young subjects were defocus and astigmatism. With this embodiment, the ability to track and optimize the image quality based on defocus was demonstrated; however, these techniques are equally applicable to astigmatism. Controllable Optical Elements (COE) capable of correcting at least one of defocus and/or astigmatism could be used in an embodiment of the invention. In another embodiment of the invention, the focus optimization method is repeated for astigmatism, or in any order of defocus and astigmatism. In other embodiments, at least one of defocus, astigmatism, and other aberrations may also be optimized.

In one of the embodiments of this invention, we propose a method to optimize the focus throughout a sample comprising scanning the sample to acquire volumetric data. This method ensures we have the highest lateral resolution OCT images through-out the sample (or specimen) even if the specimen axial extent is deeper than the depth-of-focus of the focusing beam. The method further comprises of tuning the focal position within the sample at a plurality of depths using a controllable optical element; acquiring volumetric data for each focal plane position; determining merit values at the plurality of depths for each focal position; and selecting an optimal focal position having an optimal merit value for each depth.

In another embodiment, we propose a method to acquire images comprising: identifying a tracking feature, which moves with movements of a subject; identifying a feature of interest relative to the tracking feature; tracking the feature of interest as the subject moves; and extracting an en face image relative to the feature of interest. In another embodiment, this method further comprises of the computation of a merit value by processing the en face image; and the controllable optical element is controlled to generate a plurality of merit values. In a next step, an optimal merit value is selected from a plurality of merit values; and the optimal merit value further controls the controllable optical element. A broad-band source and/or a wavelength swept light source could be used to emit light through a fibre optic beam splitter and/or a free-space beam splitter; which separates the light into two optical arms, viz., a sample arm and a reference arm.

Thus, to summarize, the en face view of OCT volumes provides important and complementing visualizations of the retina and optic nerve head investigating biomarkers of diseases affecting the retina. We demonstrate the combination of real time processing of OCT volumetric data for axial tracking. In combination with a Controllable Optical Element (COE), this invention demonstrates acquisition, real time tracking, automated focus on depth resolved en face layers extracted from a volume, and focus-stacked OCT volumes with high-resolution throughout an extended depth range.

Some of the purposes of this invention are real time axial tracking of OCT volumetric data, automated focus on a depth resolved en face layer in a tracked OCT volume corresponding to a physiological retinal layer, and extended depth-of-focus volumetric imaging. The invention is distinct relative to prior art. Prior art such as U.S. Pat. No. 9,192,295 B1, US 2013/0162978 A1 and U.S. Pat. No. 8,939,582 B1 US 20120274783 A1 and US 2015/0055093 A1 disclosed systems and methods to perform focusing in OCT imaging systems and tracking transverse eye motion. These methods require mechanical movements of the objective lens and reference arm mirror and do not relate to high resolution imaging and are not capable of placing the focus position on a specific depth-resolved layer of interest within the sample. Unlike disclosed in the prior art, we utilize a controllable optical element that is optically conjugated to the pupil (pivot) plane, which allows changing of the focal depth without any mechanical movement of the optical elements such as the lenses, and therefore does not require moving the reference arm mirror in the OCT system either. The optical conjugation of the COE with the entrance pupil of the eye also minimizes the imaging beam displacement on the pupil plane, thus enabling high resolution and wide field of view imaging. Our method of tracking retinal axial position and auto-focusing has the capability to generate high resolution depth sectioned en face (fundus) images and position the axial focal point within a specific depth layer of interest in the sample. Our method also does not require hardware in addition to the OCT imaging system for tracking, and is capable of correcting intra-volume axial eye motion in order to acquire intra-retinal layer en face (fundus) images, which are essential for high resolution imaging.

Specific embodiments of the technology have been described above for purposes of illustration, but modifications may be made without deviating from the scope of the invention. This disclosure can encompass other embodiments not expressly shown or described herein. The various advantages and features associated with certain embodiments have been described above in the context of those embodiments, but other embodiments may also exhibit such advantages and/or features, and not all embodiments need necessarily exhibit such advantages and/or features to fall within the scope of the invention.

What is claimed is:

1. A system, comprising:
   a light source to emit a light to a beam splitter, which separates the light into two optical arms, a sample arm and a reference arm;
   the sample arm further comprises of a sample, and at least one controllable optical element and light delivery optics; and
   a reference arm comprising a reference mirror;
   a light returning from the sample and reference arms combined through the beam splitter and directed towards at least one detector to generate an optical interference signal;
   an instrument control sub-system for controlling the acquisition of the interference signal;
   and the instrument control sub-system further configures the controllable optical element to automatically adjust a focus within the sample to perform extended depth-of-focus imaging.

2. The system of claim 1; wherein the instrument control sub-system constructs at least one of depth resolved images and three dimensional data sets of the sample by processing the optical interference signal in real time to guide the controllable optical element.

3. The system of claim 1; wherein the beam splitter is at least one of a fibre optic beam splitter and a free-space beam splitter.

4. The system of claim 1; wherein the light source is a wavelength swept light source.

5. The system of claim 1; wherein the instrument control sub-system further comprises of
   at least one processor configured to provide timing and control signals, and to convert the optical interference to three dimensional data sets, and to extract a specific depth layer image within the three dimensional data sets, and to calculate a merit value from the extracted depth layer image within the sample.

6. The system of claim 5 where the merit value comprises of at least one of a maximum intensity, total integrated intensity, thresholded intensity, reflection characteristics, sharpness, image gradient, and entropy.

7. The system of claim 5; wherein the processor comprises of at least one of a graphical processing unit, a central processing unit, a microcontroller, an embedded controller and a field programmable gate array.

8. The system of claim 7, wherein the controllable optical element is optically relayed to be optically conjugated to a scanning element and a pupil of the eye.

9. The system of claim 1; wherein light delivery optics further comprises of at least one scanning element.

10. The system of claim 9; wherein the scanning element is at least one of a MEMS, a galvanometric mirror, a resonant mirror, and a crystalline beam deflector.

11. The system of claim 1; wherein the light source is a broad-band light source.

12. The system of claim 11; further comprising of a spectrometer to acquire the optical interference signal.

13. The system of claim 1; further comprising of a scanning reference mirror in the reference arm to assist generating the optical interference signal.

14. The system of claim 1, wherein the controllable optical element is configured to adjust a focal plane position relative to the sample by generating phase profiles corresponding to different amounts of defocus.

15. The system of claim 1; wherein the sample is an eye.

16. The system of claim 1; wherein at least one controllable optical element has variable at least one of a focal length and an astigmatism and is at least one of a lens, a mirror, and a spatial light modulator.

17. A method to optimize a focus throughout a sample comprising:
   scanning the sample to acquire volumetric data;
   tuning the focal position within the sample at a plurality of depths using a controllable optical element,
   acquiring volumetric data for each focal plane position;
   determining merit values at the plurality of depths for each focal position; and
   selecting an optimal focal position having an optimal merit value for each depth.

18. A method to acquire images comprising
   identifying a tracking feature, which moves with movements of a subject;
   identifying a feature of interest relative to the tracking feature;
   tracking the feature of interest as the subject moves;
   extracting an en face image relative to the feature of interest.

19. The method of claim 18;
   further comprising the computation of a merit value by processing the en face image; and
   a controllable optical element is controlled to generate plurality of merit values;
   an optimal merit value is selected from a plurality of merit values;
   and the optimal merit value further controls the controllable optical element.

20. The method of claim 18 further comprising of
   at least one of broad-band source emitting light and a wavelength swept light source emitting light to
   at least one of a fibre optic beam splitter and a free-space beam splitter
   which separates the light into two optical arms, a sample arm and a reference arm.

* * * * *